United States Patent [19]
Hansen

[11] 3,956,258
[45] May 11, 1976

[54] CARCINOEMBRYONIC ANTIGENS

[75] Inventor: Hans John Hansen, Allendale, N.J.

[73] Assignee: Hoffmann-La Roche Inc., Nutley, N.J.

[22] Filed: May 13, 1974

[21] Appl. No.: 469,197

Related U.S. Application Data

[60] Division of Ser. No. 252,700, May 12, 1972, Pat. No. 3,867,363, which is a continuation-in-part of Ser. No. 133,404, April 12, 1971, Pat. No. 3,697,638, which is a continuation-in-part of Ser. No. 110,288, Jan. 27, 1971, abandoned, which is a continuation-in-part of Ser. No. 42,526, June 1, 1970, abandoned.

[52] U.S. Cl. .............................. 260/112 R; 424/88
[51] Int. Cl.² .......................................... C07G 7/00
[58] Field of Search ................................ 260/112 R

[56] References Cited

UNITED STATES PATENTS

| | | | |
|---|---|---|---|
| 3,663,684 | 5/1972 | Freedman et al. | 424/12 X |
| 3,697,638 | 10/1972 | Hansen | 424/12 |

OTHER PUBLICATIONS

Thomson et al., Proc. Natl. Acad. Sci. U.S. 64, pp. 161–167, 1969.

*Primary Examiner*—Howard E. Schain
*Attorney, Agent, or Firm*—Samuel L. Welt; Bernard S. Leon; Gerald S. Rosen

[57] ABSTRACT

Antigens associated with carcinomas and adenocarcinomas as well as methods for isolating, identifying and detecting them are disclosed.

3 Claims, No Drawings

CARCINOEMBRYONIC ANTIGENS

This is a division of application Ser. No. 252,700 filed 5/12/72, now U.S. Pat. No. 3,867,363 and which is a continuation-in-part of U.S. patent application Ser. No. 133,404, filed 4/12/71, now U.S. Pat. No. 3,697,638 which in turn is a continuation-in-part of U.S. patent application Ser. No. 110,288, filed 1/27/71, now abandoned, which in turn is a continuation-in-part of U.S. patent application Ser. No. 42,526, filed 6/1/70, abandoned, the priority date of which is hereby claimed.

BACKGROUND OF THE INVENTION

The neoplastic process in human beings has been and still is the subject of intensive study. In order to obtain a better understanding of the disease, human cancer tissue has been studied in an effort to discover the cause, treatment, prevention and/or diagnosis of cancer. Early diagnosis of cancer is very important since it increases the chances of effecting a complete remission of the disease.

In an effort to utilize known diagnostic tools to detect the presence of cancer tumors, attempts have been made to demonstrate tumor specific antigens to human carcinomas. These attempts have previously been unsuccessful with many types of carcinomas since it has not been possible to segregate normal tissue antigens from abnormal cancer antigens and demonstrate the specificity of the cancer antigens.

In the efforts to isolate abnormal cancer antigens and demonstrate their specificity, attempts have been made to cause the formation of tumor specific antibodies and demonstrate their presence in sera obtained from animals immunized with preparations of human cancer. If consistently reproducible, the demonstration of the presence of tumor-specific antibodies in animal antisera would lead to the use of a valuable diagnostic tool.

In order to fully utilize the existence of tumor-specific antibodies in animal antisera as a diagnostic tool, a test must be developed which will demonstrate the presence of the tumor antigen in the blood of the patient. Procedures which have been devised have not proven efficient or sensitive in the detection of and differentiation between carcinomas originating at different locations within the body, or metastatic conditions.

Among the possible sources of antigens associated with human carcinomas which have been most extensively studied by investigators are adenocarcinoma of the colon and digestive tract, meconium, carcinoma of the liver, ovarian cysts and carcinoma of the breast. Since adenocarcinoma of the colon is one of the most widespread cancers and usually requires a surgical procedure for definitive diagnosis, after some gross symptomatology has developed, it has been among the most extensively studied.

Efforts to extract a relatively pure antigen associated with carcinomas or adenocarcinomas have met with either no success or are impractical from a commercial point of view since a process has not been found to make it possible to completely segregagte such an antigen from normal tissue antigens and nonantigenic materials.

The presence of antigens which are stated to be specific to adenocarcinomas of the colon and digestive system by means of immunological tolerance and absorption techniques have been demonstrated, Gold et al., J. Expt. Med. 121 439–462 (1965). However, the practical and commercially feasible isolation of the antigen itself as well as its association with carcinomas and adenocarcinomas had, until the present invention, not been achieved.

The tumor-specific antigens have been previously shown to be present only in patients who have adenocarcinoma which originate in digestive system epithelium derived from embryonic entodermal tissue, i.e., esophagus, stomach, duodenom, pancreas and rectum.

It has also previously been demonstrated that the tumor-specific antigens are also present in the digestive organs of fetuses between two and six months of gestation, Gold et al., J. Exptl. Med. 122 467–487 (1965). Thus, for convenience, the antigen has been designed as carcinoembryonic antigen (CEA).

Not only has it heretofore not been possible to isolate and characterize the CEA by practical rapid methods, but it has not been possible to demonstrate its presence in the blood of persons having adenocarcinoma with a diagnostic test suitable for large screening programs.

DETAILED DESCRIPTION OF THE INVENTION

I have discovered that the material heretofore known as carcinoembryonic antigen (CEA) is a mixture of several components, at least two of which have antigenic activity which is associated with human carcinoma generally. These two active components are called carcinoembryonic antigen component A (the so-called $\beta$ antigen) and carcinoembryonic antigen component B (the so-called $\alpha$ antigen).

This invention in one significant aspect relates to a method of fractionating material having carcinoembryonic antigen activity into its component parts, e.g., carcinoembryonic antigen component A and carcinoembryonic antigen component B.

This invention in further aspects relates to methods of isolating and characterizing the carcinoembryonic antigen components associated with carcinomas, for diagnostic test procedures and for utilizing either radioactive tagged carcino-embryonic antigen material, component A or component B to detect circulating carcinoembryonic antigen material, component A and/or component B.

This invention also relates to a diagnostic test method useful in the detection of carcinoma and suitable for post-operative monitoring of carcinoma patients. "Carcinoma", as used herein, includes all carcinomas and adenocarcinomas present in humans. As used herein, "carcinoembryonic antigen material", means the material with carcinoembryonic antigen activity which contains component A and/or component B.

In order to produce radioactive tagged carcinoembryonic antigen material, component A or component B individually and utilize each separately in the improved diagnostic tests of this invention, it is first necessary to isolate and purify each entity and confirm its identity by means of specific antibodies.

According to this invention, practical processes have been discovered for:

a. Isolating, purifying, characterizing and confirming the identity and specificity of carcinoembryonic antigen material, component A and component B;

b. Utilizng radioactive tagged carcinoembryonic antigen material, component A and/or component B to detect the presence of carcinoma by the detection of circulating antigens; and c. Differentiating between circulating free and total carcinoembryonic antigen material, component A and- /or component B.

While this invention is concerned with antigens associated with carcinomas, generally the isolation and purification procedures described herein will refer to colon carcinoma tissue, metastatic liver carcinoma tissue and meconium all of which are representative of the materials containing CEA material, component A and/or component B.

Material having carcinoembryonic antigen activity is isolated and purified according to the process of this invention by homogenizing adenocarcinoma tissue from primary or metastatic tumors, preferably those originating within the digestive system, with tumors from the colon, for example, being suitable, or by homogenizing meconium.

In order to isolate the carcinoembryonic antigen material, component A and/or component B associated with the homogenized material, it is necessary to separate all other material from the homogenate, isolate the carcinoembryonic antigen material and isolate the individual components of the carcinoembryonic antigen material thereof. This is accomplished by chemical and physical extraction and purification procedures. If, for example, only component A or component B are present in the homogenate, then the isolation and purification procedures will produce the component without fractionation.

Once the extraction and purification procedures are completed, the identity of the finally isolated fractions as carcinoembryonic antigen material or a component must be confirmed. This can be accomplished by various known techniques, e.g., double diffusion in agar gel, immuno-electrophoresis, hemagglutination, passive cutaneous anaphylaxis, precipitin inhibition and the like.

In order to utilize these techniques, the antibodies used must be confirmed to be specific for the CEA material, component A and/or component B. Antibodies which meet this criteria can be produced by immunological tolerance or absorption techniques.

In the absorption technique, tumor antiserum is absorbed with normal tissue and normal fluids (saliva, serum, plasma) in order to remove antibodies produced to normal tissue components. Any residual antibody activity in the absorbed antiserum which is directed against tumor material is then considered to be tumor specific. This method is not without its faults since there is the possibility that tumor specific antibodies may have been removed or inactivated by normal tissue components similar to, but not identical with, the tumor antigens which initially stimulated the antibody production.

In the immunological tolerance technique, animals are rendered immunologically tolerant to normal tissue during neonatal life. The tolerant animals are then immunized with tumor preparations of the same donor species. Where adequate suppression of the immune response to normal tissue components has been achieved, the development of antibodies apparently specific for the carcinoembryonic antigen activity has been achieved.

Colon adenocarcinoma tumor tissue and normal colon tissue from the same individual can be utilized to illustrate this technique because adenocarcinoma of the colon almost never extends submucosally more than 6 to 7 cm. on either side of a tumor visible in the gross.

The colon adenocarcinoma tumor tissue and normal colon tissue from the same individual are treated separately but in parallel fashion. The tissue is ground up, suspended in a buffer, then homogenized. The homogenate is then treated to remove solid particles. Centrifugation or filtration through successively smaller filter openings are preferred. The purpose is to remove all particles about 0.22 $\mu$ or larger, thus removing all the bacteria present. The supernatant or filtrate is thereby sterilized to insure against bacterial contamination.

Test animals divided into appropriate groups are then immunized with the extracts and, after a suitable time interval, serum is obtained from the animals. The presence of antibodies in the test sera is demonstrated by either the Ouchterlony technique of double diffusion in agar gel, immunoelectrophoresis, hemagglutination reactions or passive cutaneous anaphylaxis. The preferred practical method, because of its simplicity and reproducible results is the Ouchterlony technique.

Once the antibodies are demonstrated to be present, it is possible to determine if a particular extraction technique does, in fact, isolate a fraction which contains carcinoembryonic antigen material, component A or component B.

I have discovered extraction and purification techniques which finally result in two separate fractions each of which invariably produces one precipitant line in the Ouchterlony technique when tested against non-absorbed antisera. The techniques, according to this invention, also provide a means wherein CEA components A and B are separated from each other and from materials of the same molecular weight and thus are isolated in substantially pure form.

CEA materials as well as components A and B are isolated and purified, according to the preferred process of this invention, from primary or metastatic carcinoma tissue. Also, CEA material as well as components A and B can be isolated and purified, according to the process of this invention, from embryonic digestive organs of fetuses in the second to seventh month of gestation and from meconiums. The following description will in most respects be directed to extraction from cancer tissue; however, the process may also apply to embryonic tissue or meconium.

CEA material, CEA component A or CEA component B in either embryonic digestive organ tissue from the first and second trimester, meconium or adenocarcinoma tissue are extracted with a glycoprotein solvent in which CEA material, component A and component B are soluble. This is required so that precipitable normal proteins and interfering antigenic materials can be separated from the CEA material or components A and B. Glycoprotein solvents which are suitable are, e.g., perchloric acid, trichloroacetic acid, phosphotungstic acid and the like. However, perchloric acid, because of its availability and ease of use is preferred.

Prior to the addition of the glycoprotein solvent, the material which is being treated is homogenized with water in order to solubilize the CEA material or component A or component B, whichever is present. The amount of water should be sufficient to solubilize all of the carcinoembryonic antigen material or component A or component B. Generally, about two liters of water per about every kilogram of treated material is sufficient. More water can be used, however, it is usually not necessary. It is preferred to use distilled water since the chances of contamination are thereby reduced. The homogenization can be carried out at from about 4°C.

to about 60°C., however, from about 4°C. to about room temperature (about 20°C. to about 25°C.) is preferred.

The solid particles are then removed from the homogenate. Since the CEA material, component A and component B are water soluble, this can be accomplished by any convenient method of separation, e.g., filtration or centrifugation and the like. Centrifugation is preferred because it is faster and sufficient force can be developed to remove substantially all the solid particles. Generally, about 3,000 to about 8,000 revolutions per minute are sufficient to accomplish this. The separation is preferably carried out at cold temperatures, e.g., about 4°C. to about 10°C., to prevent loss of activity.

The supernatant from the centrifugation is then treated with a glycoprotein solvent to remove protein materials and interfering antigenic materials.

Any temperature below room temperature is suitable for the addition of the glycoprotein solvent to the supernatant of the homogenate. Preferably, however, from about 4°C. to about room temperature is used. The temperature of the glycoprotein solvent which is added to the supernatant can also be variable, preferably, however, the same temperature as the extracting temperature is utilized. Generally, a concentrated acid is used as the glycoprotein solvent, e.g., about 0.5N to about 2N, with 2N being preferred. The solvent is added in about equal volume to the supernatant. The time in which the reaction takes place is usually about 5 to about 30 minutes. Longer times are undesirable since they can result in loss of antigenicity.

A precipitate results. This precipitate is separated from the supernatant containing the dissolved CEA material, component A or component B. Any convenient method of separation is suitable, e.g., filtration, centrifugation and the like, however, centrifugation under the same conditions as used with the homogenate is preferred.

Perchloric acid, salts such as sodium chloride and other low molecular weight materials are then removed in order to further purify the system. While it may be possible to accomplish this by precipitating the remaining proteins, I have discovered a fast, efficient method comprising dialysis through a semipermeable membrane against a polyethylene glycol with an average molecular weight of about 15,000 to 20,000 and a softening point at 60°C. A typical suitable commercial product useful for this dialysis is "20 M Carbowax" marketed by Mann Research Laboratories. The dialysis is a critical part of the process since it is fast and efficient and eliminates substantially all diffusible soluble materials except the higher molecular weight materials which include the materials containing CEA activity. The dialysis is carried out at 4°C. to 10°C., preferably 4°C. and is completed in about 18 hours. The process to this point takes about 24 hours to complete.

The use of the 15,000 to 20,000 molecular weight polyethylene glycol in the dialysis step is critical to this invention since it aids in speeding up the isolation of the CEA material, component A or component B, by the use of only one dialysis step rather than time consuming multiple dialysis steps against water and eliminates the need for lyophylizing the retentate.

The resulting retentate is substantially solid in character and contains several materials having both higher and lower molecular weights than the CEA material, component A or component B.

The separation of the portion of the resulting retentate which contains the CEA material, or component A or component B to the substantial exclusion of other materials is accomplished according to this invention by sequential chromatography with two different gel columns followed by chromatography with an appropriate ion exchange column. However, equivalent results are obtained when chromatography on the ion exchange column is used prior to the chromatography on the two different gel columns. The eluted fractions from the column chromatography which have a molecular weight of about 200,000–500,000 and a definite peak at the spectrophotometric absorption wave length of 280 m$\mu$ are those containing the CEA material, component A or component B.

The column chromatography can be accomplished by subjecting the retentate, in solution, to sequential chromatography on two different gel columns in any order. Practically, however, when using carcinoma tissue, a gel column which is used first in accordance with this invention is an agarose gel. Agarose is the neutral portion of agar. The gel material is commercially available from AB Pharmacia, Uppsala, Sweden, under the trade name "Sepharose". The gels are available as aqueous suspensions in 0.02% sodium azide as a preservative. The gel structure is due to hydrogen bonding. The gel is prepared in beaded form having a selected particle size and percent agarose. The concentration of the agarose in the gel determines its fractionation range.

The gels most suitable for use in this invention are those which have a particle size of from 40 to 210 microns and contain 6% by weight agarose. These materials named "Sepharose 6B" have a fractionation range which separates materials of molecular weight 4 $\times 10^6$ or less. In the process of this invention, Sepharose 6B is used since, when carcinoma tissue is used, it permits the separation of the fraction containing the CEA material or its components from extraneous materials of substantially higher or lower molecular weight as well as from colloidal particles.

The second column contains a gel filter material which is a hydrophilic water-insoluble cross-linked dextran polymer gel. This material and the method of its manufacture are described in British Pat. No. 854,715. The gel material, which is commercially available from AB Pharmacia, Uppsala, Sweden, under the name "Sephadex", comprises a three dimensional macroscopic network of dextran substances bonded or cross-linked together, being capable of absorbing water with swelling. The ability of the gel material to take up water is inversely proportional to the degree of cross-linkage of dextran substances in the gel material. The gel material is available in a variety of grades differing with respect to degree of porosity. The gel preferred for use in this invention when chromatography on the ion exchange column follows has an approximate molecular weight exclusion limit of 100,000, a water region (g. $H_2O$/g. dry gel) of 10 $\pm$ 1.0, a particle size of 40–120 microns and a bed volume/ml./g. dry gel of 15–20. The gel is named "Sephadex G-100". When the chromatography on the ion exchange column is first then the Sephadex preferred for use is "Sephadex G-200", having an approximate molecular weight exclusion limit of 200,000, a water regain (g. $H_2O$/g. dry gel) of 20 $\pm$ 2.0 a particle size of 40–120 microns and a bed volume/ml./g. dry gel of 30–40.

The Sephadexes are employed to further purify the fraction containing the CEA material or component A or component B. Since the columns have greater resolving power than the first column (Sepharose) for the molecular weight range of 100,000 to 200,000 for Sephadex G-100 and 150,000 to 250,000 for Sephadex G-200, further separation of the CEA material or component A or component B from lower molecular weight materials is achieved. The second column, for all practical purposes, should be used only after the colloidal particles are removed by the first column since these particles will clog the column and make it ineffective. The problem of colloidal particles is applicable to the treatment of tumor tissue. However, when, for example, meconium is used, it is preferred to use the Sephadex G-100 or G-200 column first since it removes bile salts. After the removal of the bile salts, then the Sepharose 6B column is advantageously used.

In the preferred process the chromatography is accomplished by dissolving the retentate in aqueous buffer at a pH of from about 5 to 9, preferably pH 7. A typical suitable buffer composition useful in the process of this invention is composed of 0.1 M Tris-OH made in 0.135 M NaCl, adjusted to pH 7 with HCl to which 0.02% of sodium azide is added as a preservative. The thus-formed buffer solution is then run through the first column, eluted with the same buffer solvent and the eluates collected. The eluates are then dialyzed against the polyethylene glycol as described above. The collected active fractions are then redissolved in an aqueous Tris-OH buffer of pH 5 to 9 of the same composition as described above, the solution is run through the second column, eluted with a buffer of pH 5 to 9 of the same composition as described above and the active fractions are collected and dialyzed as before.

The advantage of utilizing low temperatures, i.e., from about 4°C. to about 10°C. is that it maintains stability and can result in increased resolution. The fractions collected from the second column are those which have a molecular weight of 200,000–500,000 and have a reading with a peak at 280 m$\mu$ on a UV spectrophotometer. Those fractions collected from the first column are selected based on the same criteria, however, they contain material slightly greater and slightly less (as low as 70,000 MW) than 200,000–500,000 MW. The collected fractions contain the CEA material or component A or component B depending on the origin of the treated material. This is shown by either the precipitin inhibition or direct Ouchterlony testing against unabsorbed tumor antiserum. A single line precipitate indicates pure CEA activity.

The active fraction from the second gel column is then subjected to chromatography on an ion exchange column in order to further purify and fractionate the CEA active fraction and separate it from other materials which are present. I have found that in most cases the fraction containing the CEA activity which is derived from colon adenocarcinoma tissue from the second gel column contains three different materials (unless, as in some cases of colon adenocarcinoma, only component A or component B are present singly), all having molecular weights between about 200,000 and 500,000. Of these materials, one comprising about 5% by weight of the fraction is non-reactive. A second material, comprising about 10% by weight of the fraction has antigenic sites which react with the CEA specific antibody and is identified here as CEA component B. A third material, comprising about 85% by weight of the fraction also has antigenic sites which react with the CEA specific antibody and is identified here as CEA component A.

It has also been found that other materials, e.g., meconium, lung tumors, breast tumors, have different proportions of the components and as a general rule these amounts vary from patient to patient and from tumor to tumor. Meconium, for example, has only component B.

In order to obtain the pure CEA components it has been found necessary to utilize an ion exchange column. If only one component is present, then the ion exchange column is used to purify it and confirm its presence as the sole CEA active material present.

The ion exchange column found suitable for use in accomplishing the desired separation is a mixed bed column composed of a cation exchanger, carboxymethyl cellulose, and an anion exchanger, diethylaminoethyl cellulose.

The carboxymethyl celluloses most suitable for use in this invention are those which are microgranular in form, have rod shaped particles with a particle size distribution expressed as diameter of equivalent spheres within a range of about 20 $\mu$ to about 60 $\mu$, have a capacity of 1.0 ± 0.1 meq./gm. and a water regain of 2.3–2.7 gm./gm. dry exchanger. The preferred ionic form is the $Na_+$ form. A suitable ion exchanger is commercially available in a preswollen form from H. Reeve Angel Inc., Clifton, New Jersey, under the trade name "CM 52".

Another suitable carboxymethylcellulose is "CM 32". This does not have the capacity per volume of CM 52 but is otherwise similar, i.e., it is microgranular in form, has rod shaped particles with a particle size distribution expressed as diameter of equivalent spheres within a range of 20 $\mu$ to 60 $\mu$, has a capacity of 1.0 ± 0.1 meq./gm. and a water regain of 2.3–2.7 gm./gm. dry exchanger. "CM 32" is available in dry form from H. Reeve Angel Inc., Clifton, New Jersey.

The diethylaminoethylcelluloses most suitable for use in this invention are those which are microgranular in form, have rod shaped particles with a particle size distribution expressed as diameter of equivalent spheres within a range of about 20 $\mu$ to about 60 $\mu$, have a capacity of 1.0 ± 0.1 meq./gm., a water regain of 2.3–2.8 gm./gm. dry exchanger and are in the free base form. A suitable ion exchanger is commercially available from H. Reeve Angel Inc., Clifton, New Jersey under the trade name "DE 52".

The mixed column is produced by removing the fines from each exchanger by, for example, aspiration of the supernatant resulting from adding a 10-fold volume of water, stirring and allowing to settle. Subsequently, a solution made from ammonium acetate in 1.0 M sodium chloride is added to each column and equal volumes of each of the resulting slurries are then combined and poured in a 2.5 × 40 cm. column to give a 2.5 × 18 cm. mixed column.

The eluate from the gel columns is dialyzed against the polyethylene glycol as described above. The resulting material is then dissolved in an aqueous buffered solvent which solubilizes proteins and does not have affinity for the column.

A typical suitable solvent is ammonium acetate at pH 4. The buffered ammonium acetate solvent can be formed by adjusting the pH of 0.1 M acetic acid with ammonium hydroxide.

The resulting solution is then clarified. The preferred clarification method is centrifugation which effectively removes all the undissolved particles. High speed centrifugation is most effective for this clarification, preferably at speeds which produce at least 100,000 times gravity.

The resulting supernatant is then applied to the mixed bed ion exchange column and eluted with an ammonium acetate-sodium chloride eluant at pH 4. Other alkali metal chloride salts such as potassium chloride are also suitable. The relative amounts of ingredients in the eluant compositions are varied. The variations in the composition results in a fine separation of the active fraction into its major components and numerous minor components. This is accomplished by utilizing compositions containing the ammonium acetate solvent in 0.05, 0.1, 0.25 and 1.0 M sodium chloride solutions. The specific relationship of the ammonium acetate to the sodium chloride is interrelated to the pH of the system, thus, if a different pH is utilized, then the relationship must be changed to accomplish the same purpose. The identity and relative amounts of the major components varies with the identity of their source. For example, in a typical case wherein colon carcinoma is the source of antigen activity, about 85% by weight of the material present in the active fraction is eluted when the eluant contains ammonium acetate in 0.05 M sodium chloride. This is CEA component A. About 10% by weight of the material present in the active fraction is eluted when the eluant contains ammonium acetate in 0.1 M sodium chloride. This is CEA component B. The remaining material is eluted when the eluant contains ammonium acetate in 0.25 M sodium chloride. In cases wherein only component A is present or only component B is present, then the component present will be eluted with the eluants as described for each component.

An alternative method of producing carcinoembryonic component A and/or component B takes advantage of the fact that it is easier to scale up for production the Sepharose and Sephadex columns than the mixed bed columns.

The alternative method involves first chromatographing the perchloric acid tumor extract on a mixed bed ion exchange column. The mixed bed column suitable for use is one composed of DE 52 and CM 52 made as described above. In the event both component A and component B are present in the tumor extract, they are eluted separately as described above, i.e., component A is eluted in solutions having 0.05 M sodium chloride and component B is eluted in solutions having 0.1 M sodium chloride. The resulting active components are then chromatographed on two different gel columns, the described Sepharose columns preferably Sepharose 6B followed by chromatography on a Sephadex column. While Sephadex G-100 is suitable, Sephadex G-200 provides greater differentiation.

The resulting products are chemically, immunologically and electrophoretically identical to those resulting from the other process described herein.

In addition to having the same electrophoretic characteristics as CEA material, i.e., migrating anodally 10–14 cm. in block electrophoresis at the same time as ferritin marker migrates 18 cm. anodally, using 400 volts and about 20mA with a borate buffer of pH 8.6 and ionic strength 0.05, CEA component A has a molecular weight of between 120,000 and 240,000, is eluted from a mixed bed ion exchange column having the composition as described with an ammonium acetate-sodium chloride eluant at pH 4 wherein the eluant contains ammonium acetate in 0.05 M sodium chloride. Component A also forms a single line precipitate with its specific antibody in unabsorbed antiserum in gel diffusion tests, is soluble in perchloric acid and has a spectrophotometer absorption peak wave length of 280 m$\mu$.

Also, CEA component B in addition to having the described electrophoretic characteristics of CEA material has a molecular weight of between 120,000 and 240,000, is eluted from a mixed bed ion exchange column having the composition as described with an ammonium acetate-sodium chloride eluant at pH 4 wherein the eluant contains ammonium acetate in 0.1 M sodium chloride. Component B also forms a single line precipitate with its specific antibody in unabsorbed antiserum in gel diffusion tests, is soluble in perchloric acid and has spectrophotometer absorption peak wave length of 280 m$\mu$.

Chemical analysis of component A and component B reveals that they differ somewhat in the amounts of amino acids and monosaccharides, for example, component B has nearly twice as much L-fucose as component A and about two and one-half times as much sialic acid. Further, there are minor differences in the chemical analysis of the components when derived from different sources. Typical analyses of the products produced by the processes of this invention are as follows:

| Amino Acid | $\mu$ Moles Amino Acid or Monosaccharide Per 100 $\mu$ Moles Total Amino Acid | |
|---|---|---|
| | CEA Component A | CEA Component B |
| Aspartic Acid | 15.56 | 14.00 |
| Threonine | 9.19 | 8.80 |
| Serine | 12.52 | 11.20 |
| Glutamic Acid | 10.52 | 12.80 |
| Proline | 5.10 | 5.20 |
| Glucine | 6.77 | 6.40 |
| Alanine | 5.53 | 6.40 |
| Valine | 7.16 | 7.20 |
| Isoleucine | 5.24 | 4.80 |
| Leucine | 8.97 | 8.80 |
| Tryosine | 4.00 | 4.00 |
| Phenylalanine | 1.97 | 2.40 |
| Lysine | 2.37 | 2.40 |
| Histidine | 1.64 | 2.40 |
| Arginine | 3.10 | 4.00 |
| L-Fucose | 10.1 | 17.2 |
| D-Mannose | 16.4 | 19.6 |
| D-Galactose | 13.0 | 23.6 |
| N-Ac-D-Glucosamine | 25.9 | 38.8 |
| Sialic Acid | 3.7 | 10.4 |

The material or components containing CEA activity are determined by either the precipitin inhibition or direct Ouchterlony test against unabsorbed tumor antiserum. A single line precipitate indicates pure CEA activity. Thus, any material which forms a single line precipitate with unabsorbed CEA anti-serum by either the precipitin inhibition or direct Ouchterlony technique of double diffusion in agar gel is included within the scope of this invention and is suitable for use in the diagnostic tests described herein.

In order to utilize these techniques, the antibodies used must be confirmed to be specific for CEA material, component A and/or component B. Antibodies which meet this criteria can be produced by immunological tolerance or absorption techniques as mentioned above.

Once the antibodies are demonstrated to be present, it is possible to determine if a particular extraction technique does, in fact, isolate carcinoembryonic antigen material, component A or component B. Using these techniques, I have found that when the CEA material is present, component A and component B respectively, obtained from the mixed bed ion exchanger contains substantially all the CEA activity present in the CEA active fraction. The component which is preferred for use in the radioimmunoassay of CEA is component B. However, either the CEA material or component A can be satisfactorily utilized.

In another aspect of this invention, I have discovered radioimmunoassay techniques which are simple to perform and have a high degree of reproducibility and specificity.

In radioimmunoassays, it is important that the radioactive atom be sufficiently reactive with the molecule to be tagged to provide an adequate concentration of radioactivity for determination and the radioactive atom must provide a sufficient number of disintegrations per unit of time to provide sufficient sensitivity for accurate determinations. Further, in the case of radioimmunoassay of antigens, the antigenicity must not be deleteriously affected by the conjugation of the radioactive atom to the antigen.

By means of the present invention, it is possible to detect the existence of human carcinoma growth by assaying a circulating tumor associated antigen. This invention provides a test sufficiently sensitive to detect at least 1 ng. of CEA material, component A or component B per ml. of serum or plasma. This sensitivity has been found sufficient to detect abnormal amounts of CEA activity, considered in most cases to be 2.5 ng. or more. A very minor amount, e.g., less than 0.05 ng. of CEA activity may be present in normal situations. The sensitivity of the assay is limited only by the specific activity of the radioactive atom.

The CEA material, component A or component B can be tagged with radioactive atoms which will react with their chemically reactive groups and not substantially diminish their antigenicity. $I^{125}$ has been found to be a particularly suitable radioactive atom.

The CEA material, component A or component B can be radioiodinated by methods known in the art, with minor modifications to concentration and volumes. The Chloramine T method of Hunter and Greenwood, Biochem. J. 91, 46 (1964) using iodine 125 is particularly useful.

A radioiodination efficiency of about 20% to 50% can be obtained by the process described herein. The radioiodination process is equally applicable to the CEA material which is purified and isolated prior to its fractionation into components A and B, or each of the components. Preferred for use in this invention, however, is component B.

The reaction is effected, for example, by using a 200 $\mu$l. reaction mixture containing 100 $\mu$g. of Chloramine T (sodium p-toluenesulfo-chloramine); 0.025–0.4 mg. of CEA material or an individual component thereof and 4 mCi of $I^{125}$ in the form of KI or NaI. The reaction takes place in about 1 minute at room temperature and is stopped by the addition of sodium metabisulfite. The function of the Chloramine T is to oxidize the iodide salt to iodine. The function of the sodium metabisulfite is to reduce unreacted $I^{125}$ back to its salt. Other reducing agents can also be used, e.g., potassium metabisulfite. The oxidizing and reducing agents used should not be so strong that they damage the antigenicity of CEA material or its components. The radio-iodinated product can be separated from residual $I^{125}$ by chromatography in a cross-linked dextran gel column, e.g., Sephadex G-100, and removing the tube with the greatest radioactivity in the first peak. The resulting product has a specific activity of between about 1,000–25,000 dpm./ng., preferably between about 10,000 and 20,000 dpm./ng., i.e., about 5–10 m$\mu$ Ci/ng. of CEA material, component A or component B.

It is necessary, in order to achieve success in the aforesaid diagnostic technique, to treat the patient's blood in a manner which will insure that all the CEA material, component A or component B, to the exclusion of interfering materials, is in the finally used serum or plasma. This can be accomplished by treating blood serum or plasma from the patients with a glycoprotein solvent which solubilizes the CEA material, component A or component B, and then clarifying the resulting solution. It has been found that both serum and plasma from the blood of patients are suitable for use in this process, however, plasma is preferred.

The glycoprotein solvent which has been found suitable for this process is perchloric acid. Perchloric acid of 1.2 M or a sufficient amount to provide a concentration of about 0.6 M or less of perchloric acid is the preferred solvent since it removes interfering substances, frees antigenic sites and lowers ionic strength. The resulting solution containing dissolved CEA material, component A or component B, if any are present, is then clarified. The preferred clarification method is to centrifuge, collect the supernatant and dialyze against distilled water, then against buffered water (pH 6–6.25, ammonium acetate with 0.01 M acetate). This usually takes about 6 to 10 hours. The dialysis residue (retentate) can then be dried by lyophylization, this is not essential however. By using this method a purified extract containing greater than about 95% of the CEA material, component A or component B originally present is produced.

It is important to this process that the extract is treated as described since the glycoprotein solvent which solubilizes the CEA material, component A or component B in the initial step dissociates any pre-existing CEA-anti-CEA complexes and activates the antigenic sites in the patient's serum or plasma, enabling the recovery of substantially all the CEA activity originally present. This provides a method for detecting CEA activity in patients with primary carcinomas and metastatic carcinomas of varying origin.

It is also possible in another aspect of the radioimmunoassay techniques of this invention to add the antibody directly to the dialyzed supernatant resulting from the glycoprotein solvent extract of the patient's blood serum or plasma. This eliminates the need for time consuming lyophylization procedures and provides a method for detecting CEA materials, component A and/or component B in patients having carcinoma.

It is further possible in a preferred aspect of the radioimmunoassay techniques of this invention to treat the blood serum or plasma by diluting in such a manner that its ionic strength is reduced, then add the antibody directly to the dilution.

The dilution can be accomplished by adding at least 100 volumes of either water or a salt solution of low ionic strength to each volume of the blood serum or plasma. It is preferred to use plasma. Generally any convenient salt can be used as long as it does not interfere with the subsequent treatment with zirconyl phosphate. The salts found suitable are, for example, ammonium acetate, sodium chloride, sodium borate (pH 8.4) and the like. Ammonium acetate of 0.01 M or less is preferred.

The dilution of the blood serum or plasma is for the purpose of lowering the ionic strength of the solution in order to free or activate antigenic sites of any free CEA material or component which is present. This technique does not dissociate any pre-existing CEA-anti-CEA complex but makes possible detection of free circulating CEA activity. It is important when using salt solutions as the diluent, that the molarity of the salt be sufficient to lower the ionic strength of the serum or plasma to a level which will activate the antigenic sites.

Since no dialysis procedures are required, this procedure saves considerable time and is suitable for initial screening procedures to detect free circulating CEA activity.

Further, in order to effectively conduct the radioimmunoassay, a supply of antibodies specific to the CEA material, component A and/or component B must be assured. This is accomplished by immunizing animals with the purified CEA material or a component in conventional manner as follows.

An emulsifier, e.g., Freunds adjuvant (complete) is added to the CEA material or either component in a saline solution. The emulsion can be injected in animals intramuscularly, subcutaneously, in the foot pad or any combination of these methods. Animals such as fowl, rabbits, horses, goats, sheep and the like are suitable. The regimen in rabbits, for example, is injections twice a week until five injections are made. After the last injection, blood is collected from the animal. The serum from this blood is unabsorbed CEA antiserum.

In one method, 400 $\mu$g. of CEA material or a component in 1 ml. saline solution (0.9%) is utilized. The injection is made intramuscularly using a volume about four times that injected in the foot pad.

The antibody present in the antiserum, after absorption with normal tissue components, is specific in its activity against the CEA material, component A and/or component B to the exclusion of other antigens.

In conducting the radioimmunoassay of CEA, procedures based on both the techniques of isotope dilution and competitive-inhibition can be used. However, the competitive-inhibition method is the preferred method of this invention. In these methods, a titration curve, then a standard inhibition curve are obtained.

The standard inhibition curve can be made by the Farr procedure. It is a measure of the complex formation with specific antibodies. The curve reflects the amount of CEA material, component A and/or component B present per unit of serum. The measurement is in nanograms per ml., which is plotted against a known percentage of radioactive tagged CEA material, component A or component B. The resulting curve is used to plot the amount of CEA material, component A or component B in a patient's serum.

In a preferred method, a standard inhibition curve can also be obtained by the competitive-inhibition method by adding standard CEA material, component A or component B to a series of tubes containing powdered perchloric acid extract of normal human serum or plasma. A measured amount of CEA antiserum which had previously been determined from a standard dilution curve is added to the series of tubes containing a dialyzed perchloric acid extract of normal blood serum or plasma described above, or alternatively serum or plasma diluted with 0.01 M (0.01 N) ammonium acetate buffer at pH 6–6.25. In this alternative method wherein the test fluid is diluted, a maximum normality of buffer should not be greater than 0.01. Lower normalities are suitable. Where appropriate, molarity can be used to describe the concentration, equivalent normalities can be calculated by conventional means.

The resulting solutions are incubated at about 45°C. for a sufficient time to complete the reaction, usually about 30–45 minutes is sufficient. Following the incubation, a measured amount of radioiodinated CEA material, component A or component B is added to each of the tubes. The incubation is then continued for about an additional 30 minutes at about 45°C. When the incubation is completed, a precipitant which precipitates the antibody and antigen-antibody complex but not the antigen, is added to the solution to coprecipitate the antibody bound CEA material, component A or component B. Preferably, a zirconyl phosphate gel is used.

Under the conditions described above, free CEA material, component A or component B remains in solution, $I^{125}$ content of the precipitate or supernatant is then determined from a reading on a suitable instrument and the amount of CEA material, component A or component B in the serum or plasma is then determined by reference to a standard.

The assay performed on the powdered perchloric acid extracts of serum or plasma processed in the same manner as the standard CEA material, component A or component B, results in a determination of the amount of CEA material, component A or component B in the patient's blood. This in turn is indicative of the presence or absence of carcinoma in the patient.

According to this invention, the radioimmunoassay can be accomplished by either a routine isotope dilution procedure or the competitive-inhibition assay method described above.

The isotope dilution assay method is carried out by adding a measured amount of tagged CEA material, component A or component B to a perchloric acid extract of blood serum or plasma which is then dialyzed. The extract is then neutralized with, e.g., NaOH, and a measured amount of antibody is added. The mixture is then dialyzed against the polyethylene glycol described previously, driving the antibody-antigen reaction to completion.

The resulting precipitate is then dissolved in boric acid buffer at pH 6.25. The radioactivity is then determined by adding zirconyl phosphate gel to the solution, then centrifuging and assaying the precipitate for radioactivity.

The preferred competitive-inhibition assay method described above is carried out by dissolving the solid perchloric acid blood serum or plasma extract in a suitable buffered solvent at a pH of 5–8, preferably 6.25. While any conventional buffer is suitable, e.g., phosphate buffer, I have found that buffered solvents containing boric acid are preferred. This is surprising since heretofore borate buffers have been considered unsuitable for use in radioimmunoassay or isotope dilution assay at an acid pH. The use of acidic conditions is dictated by the fact that the CEA material, component A or component B are not sufficiently stable at neutral or alkaline pH's to maintain their antigenicity.

A measured amount of antibody is then added to the solution. While any amount is suitable, 30 units is used for convenience and ease of measurement, however, from about 30 to about 300 units are suitable.

A unit of CEA activity is a nanogram of CEA material, or the equivalent amount of component A or component B. A unit of antibody is the amount of antibody which is bound by a nanogram of CEA material, or the equivalent amount of component A or component B.

The resulting mixture is then incubated for about 24 hours. 50 Units of tagged CEA material or the equivalent amount of component A or component B are then added and the mixture is again incubated for about 24 hours. It is possible, however to use from about 20 to about 500 units, however, 20–50 units have been found to be preferred. If there is some CEA material, component A or component B in the serum or plasma, then the amount of unreacted tagged CEA material, component A or component B in the serum or plasma can be determined either qualitatively or quantitatively. The radioactivity is determined by adding zirconyl phosphate gel to the solution, then centrifuging and assaying the precipitate for radioactivity.

In another preferred aspect of this invention, the assay for determining free circulating CEA material, component A or component B is carried out by diluting either blood serum or plasma with at least 100 volumes of water or a low ionic salt solution as described previously.

The solution is then transferred into suitable test tubes, 30 units of CEA antiserum are added and the mixture is incubated at about 45°C. for 30–45 minutes. 20 to 50 nanograms of radio-iodinated CEA material or equivalent amounts of component A or component B, having 10,000 to 20,000 dpm./ng. are then added and the mixture is incubated for about 30 minutes at about 45°C. If there is some free CEA material, component A or component B, in the blood serum or plasma then the amount of unreacted tagged CEA material, component A or component B in the blood serum or plasma can be determined either qualitatively or quantitatively. The radioactivity is determined by adding zirconyl phosphate gel to the solution, then centrifuging and assaying the precipitate for radioactivity.

The method is advantageous because it takes about 2 hours to complete. It is suitable for determining only the free CEA activity. When used in conjunction with the competitive-inhibition assay methods, it is possible to have large scale screening for carcinomas.

The following examples illustrate the invention.

EXAMPLE 1

150 Grams of frozen primary colon adenocarcinoma tumor was homogenized in 5 volumes of distilled water at 5°C. for 2 minutes in a homogenizer. The homogenate was then blended for about 5 minutes in a blender. The resulting material was then centrifuged for 30 minutes at 5,000 rpm. The supernatant was decanted and a stick was used to prevent the top fat pad which forms from breaking and contaminating the solution. One volume of 10% perchloric acid was added to the supernatant and stirred at 5°C. for 10 minutes. The resulting mixture was centrifuged for 30 minutes at 5,000 rpm. The supernatant was decanted and filtered through glass wool. The resulting filtrate was then dried by dialysis against a 20 M Carbowax solution which was prepared by filling a 10 liter beaker with 20 M Carbowax Flakes and filling it to the 7 liter mark with a borate buffer at pH 8.4, then stirring until the flakes dissolved. The resulting solid dissolved in 8 ml. of Tris(hydroxymethyl)-aminomethane-NaCl (Tris-NaCl) solution. The resulting solution was centrifuged for 30 minutes at 105,000 gravity and 5 ml. of the resulting supernatant was applied to a Sepharose 6B column and eluted with the Tris-NaCl solution using 80 drops per tube collected in 5 ml. fractions at the rate of 0.5 ml./minute. Tubes 45–57 were pooled and concentrated by dialysis againt 20 M Carbowax. The resulting concentrate was then applied to a Sephadex G-100 column. This was eluted with the Tris-NaCl solution and 4 tubes containing 5 ml. each of the first peak were pooled and dried by dialysis against 20 M Carbowax. The resulting solid material was dissolved in 2 ml. of the Tris-NaCl solution and 1 ml. was labelled with $I^{125}$ by conventional means. The $I^{125}$ labelled material was applied to a Sepharose 6B column and eluted with the Tris-NaCl solution. The pooled fractions 45-57 were frozen in 5 ml. tubes and stored at −20°C. This is called Tumor Extract No. 1 (TE-1). When studied by gel diffusion versus goat antiserum, a single strong band appeared. In certain tumor extracts a second minor band appeared.

2 Ml. of labelled TE-1 were applied to a CM-52:DE-52 column in 50 ml. of ammonium acetate (pH 4) solution and the column was washed with 150 ml. of ammonium acetate. Almost all the $I^{125}$ was retained by the mixed cellulose celluose exchange column. The column was then eluted with 500 ml. each of ammonium acetate-NaCl solutions containing 0.05 M NaCl, 0.1 M NaCl, 0.25 M NaCl, 1.0 M NaCl. Two peaks were eluted with the 0.05 M NaCl-buffer. The first peak is that of CEA component A. The second peak appeared to be degraded 120,000 molecular weight material which is called M-120. A second major peak was eluted with the 0.1 M NaCl-buffer and is a pure material having 240,000 molecular weight, it is CEA-component B. A third major peak was eluted with the 0.1 M NaCl-buffer and was not reactive with the antisera. This indicates it is probably a normal component. Thus, the first peak which was eluted with the 0.05 M NaCl is CEA component A which contains CEA activity. The second major peak, CEA component B, also contains the CEA activity. The identity of the CEA material, component A and component B is confirmed by its forming a single line in the Ouchterlony gel diffusion test with unabsorbed antiserum. When subjected to block electrophoresis using Sephadex G-25 Fine [a cross-linked dextran gel having an approximate molecular weight exclusion limit of 5,000, a water regain (g$H_2O$/g. dry gel) of 2.5 ± 0.2, particle size of 20–80 microns and a bed volume/ml./g. dry gel of 5] on a non-conductive block, e.g., Lucite, the CEA material, component A and component B behave identically as follows:

The block electrophoresis medium, Sephadex G-25 Fine is swollen with water for 2 hours at 80°C. and washed by decantation with borate of pH 8.6 and ionic strength 0.05, then suction filtered through a sintered glass disk.

A thick slurry of the gel is poured onto a Lucite block support of 61 cm. × 7.5 cm. × 1 cm. in dimensions and allowed to distribute itself evenly along the plate to a depth of 1 cm. The surface is then blotted with cotton gauze sponges until firm but not completely dry.

The block is then fitted with 3 mm. chromatography paper contacts (Whatman) all aligned in the same direction of flow of the paper. The block is then placed in the electrophoresis apparatus and allowed to equilibrate for 1 hour under the operating conditions of 400 volts, with a constant current of approximately 20 mA at 4°C. A 1 cm. strip is then removed from the center of the block and mixed well with a solution of 60 mg. of CEA material produced as above, in 0.5 ml. of 0.05 M borate. The resulting slurry is then poured back in the central strip. One to two drops of ferritin (6 × recrystallized) at a concentration of 100 mg./ml. is then spotted at the cathodal extremity of the block. 24 Hours after the start of the run, the ferritin marker moves 18 cm. anodally. At that time the block is removed from the electrophoresis apparatus and 2 centimeter strips between the zone of application and the anodal extremity are eluted with 2 M NaCl passed through 0.20 $\mu$ disposable grid membrane (Nalgene). The activity is localized 10–14 cm. anodal to the application zone with weaker activity being found 8–10 cm. anodal to the application zone.

When components A and B are treated separately in the same manner, identical results are obtained.

EXAMPLE 2

500 G. of metastatic liver adenocarcinoma tumor was homogenized in 2 volumes of deionized water at 4°C. for 3 minutes in a homogenizer. The resulting homogenate was centrifuged at 7,100 times gravity for 20 minutes. The supernatant was removed by decantation. The supernatant was made 0.6 M with respect to perchloric acid by adding an equal volume of 1.2 M perchloric acid and mixing for 20 minutes at 4°C. The resulting mixture was centrifuged for 30 minutes at 5,000 rpm. The resulting supernatant was collected and neutralized to pH 7.0 by the slow addition of concentrated ammonium hydroxide, with mixing. The resulting mixture was exhaustively dialyzed against deionized water. The dialysis extract was concentrated by ultrafiltration with an XM-300 membrane to a volume of less than 50 ml. Any particulate matter remaining was removed by centrifuging the concentrated extract at 91,000 times gravity for 60 minutes.

The resulting supernatant was chromatographed at pH 4 on a mixed bed ion exchange resin and eluted with a discontinuous sodium chloride gradient. The mixed bed ion exchange resin used was the same one utilized in Example 1, i.e., CM-52:DE-52. The process for the mixed bed chromatography was the same as utilized with labelled TE-1 as set forth in Example 1. The active fractions in the 0.05M and 0.1 M sodium chloride eluents were each separately concentrated and dialyzed to a volume of 4–6 ml. by ultrafiltration using a UM-10 membrane. Each of the fractions were then further fractionated by gel filtration by chromatographing on a Sepharose 6B column in the same manner as set forth in Example 1. The resulting concentrates of each fraction from the 211–295 ml. fraction were concentrated and dialyzed by ultrafiltration to a volume of 15 ml. and then applied to a Sephadex G-200 column using the same process as set forth for the Sephadex G-100 column in Example 1. The resulting products were CEA component A which was eluted with 0.05 M NaCl and CEA component B which was eluted with 0.1 M NaCl. These materials were each subjected to electrophoresis and further analyzed immunologically and chemically and found to be identical to the materials prepared in Example 1 and identified respectively as component A and component B.

EXAMPLE 3

Six 5 ml. tubes containing normal serum and six 5 ml. tubes containing serum from suspected colon cancer patients each were extracted with an equal volume of 1.2 to 2 molar perchloric acid by shaking for 20 minutes and then centrifuging at 8,000 gravity for 5 minutes at 5°C. The supernatants were collected and transferred to a dialysis tubing and placed in a 250 ml. beaker containing a Carbowax solution formed by filling a 10 l. beaker with 20 M Carbowax Flakes and then filling the beaker to the 7 liter mark with borate buffer of pH 8.4 and stirring until the flakes dissolve. After 5 hours of dialysis, the resulting precipitate in the tubes was dissolved in 1 ml. of borate buffer at pH 6.25 and transferred to 15 × 125 mm. test tubes. 0.1 Ml. of normal human serum was added to each tube and mixed. To each of the six tubes containing normal serum and the perchloric acid extract, 0, 10, 50, 100, 250 and 500 nanograms of CEA was added. Then 300 to 500 units of CEA antisera was added to each of the 12 tubes and mixed. The tubes were then stored in an icebox at 5°C. for 12 hours. Subsequently, 500 units of CEA-$I^{125}$ was added to each tube and incubation was continued for 18 hours at 5°C. Five ml. of zirconyl phosphate gel was added to the tubes and the tubes were then filled with ammonium acetate buffer at pH 6.25. The tubes were stopped with rubber stoppers, inverted five times and centrifuged at 1500 gravity for 5 minutes. The resulting supernatant was then discarded. The solid gel which remained was washed with an ammonium acetate buffer by filling the tubes with the buffer and dispersing the gel with a mixer, then centrifuging at 1500 times gravity for 5 minutes. The gel was assayed for bound $I^{125}$ with a Packard 3003 Tri-carb Scintillation spectrometer. Other similar equipment can also assay for the bound $I^{125}$. The results of the serum being tested for CEA activity were compared to the standard and the amount of CEA material, component A or component B in the unknown sera was determined.

EXAMPLE 4

0, 10, 50, 100 and 500 Nanograms of CEA material standard were added to separate tubes each of which contained 5 ml. of normal sera and then mixed. The standards and serum from suspected cancer patients were extracted wtih perchloric acid, centrifuged and dialyzed against 20 M Carbowax in the same manner as in Example 3. The resulting precipitate was dissolved in 1.0 ml. of borate buffer of pH 6.25, then 500 units of radioactive tagged CEA material was added, the mixture was mixed thoroughly and then 300 units of CEA antisera were added. The mixture was dialyzed against a fresh 20 M Carbowax solution and brought to dryness in about 2 to 3 hours. The resulting precipitate was dissolved in 1 ml. of borate buffer of pH 6.25 and then 5 ml. of zirconyl phosphate gel were added. The assay for the $I^{125}$ was made according to the process set forth in Example 3.

EXAMPLE 5

Human meconium is homogenized in 3 volumes of 10% perchloric acid at 5°C. and centrifuged at 4,000 rpm for 30 minutes. The supernatant is then dialyzed against 20 M Carbowax.

The precipitate is taken up in a minimum volume of Tris-NaCl solution of pH 7 and centrifuged at 105,000 g. for 30 minutes.

5 Ml. of the supernatant is then applied to a Sephadex G-100 column and eluted with Tris-NaCl solution. Four tubes of 5 ml. each from the first fraction were pooled and brought to dryness by dialysis against 20 M Carbowax. The residue is taken up in 8 ml. of NaCl-Tris solution and centrifuged at 105,000 g. for 30 minutes. 5 Ml. of the resulting supernatant is then applied to a Sepharose 6B column and eluted with the Tris-NaCl solution using 80 drops per tube collected in 5 ml. fractions at the rate of 0.5 ml./minute. Tubes 45–57 were pooled and brought to 1 ml. by dialysis against 20 M Carbowax. When studied by gel diffusion versus goat antiserum, one strong band developed. It was identical to CEA component B.

EXAMPLE 6

Carcinoembryonic antigen (CEA) material was isolated and radiolabelled with $I^{125}$ as described in Example 1.

A goat antiserum mono-specific for CEA material was reacted with radiolabelled CEA material to form an antibody-antigen complex. The excess radiolabelled CEA material was separated from the complex by adsorbing the complex with zirconyl phosphate gel (pH 6.25) as described in Examples 3 and 4.

The radiolabelled CEA was then incubated with the antiserum to illustrate the ion sensitivity of the antigen-antibody reaction as follows:

100 Ng. of radioiodinated CEA material was incubated with antiserum diluted with water (1–10,000) at 45°C. for 30 minutes in 1 ml. each of normal serum (goat, human, rat, rabbit), 0.15 M NaCl, 0.075 M $Na_2HPO_4$, 0.15 M Tris-Hcl (pH 7.5) and 0.1 M ammonium acetate. This resulted in minimal complex formation.

When the radioiodinated CEA material and the antiserum were incubated in 1 ml. each of $H_2O$, 0.01 M NaCl, 0.01 M ammonium acetate 1% normal serum diluted in $H_2O$, or 0.05 M sodium borate (pH 8.4) antigen-antibody complex formation took place.

The antiserum also formed a complex with the radioiodinated CEA material when incubated in 10 ml. of 0.01 M ammonium acetate, 0.1 ml. of normal serum diluted to 10 ml. with water, or 0.005 M sodium borate (pH 8.4).

10 Ng. of CEA material added to dialyzed supernatant from 5 ml. of normal serum and 5 ml. of 1 M perchloric acid, neutralized 10% of the antiserum when incubated at 45°C. for 30 minutes prior to the addition of measured amounts of radioiodinated CEA material.

CEA material was detected in 28 of 30 perchloric acid extracts of serum obtained from patients with colon adenocarcinoma and directly in sera of metastatic patients after dilution of 0.1 ml. serum in 10 ml. of water. This indicates that dilution which weakens the ionic strength of the serum provides access to an antigenic site on the CEA material.

EXAMPLE 7

A 3 ml. aliquot of 2 M perchloric acid was added to 5 ml. aliquots of serum or plasma while agitating in a mixer. The mixtures were allowed to stand at room temperature for 15 minutes then mixed again and allowed to settle. The mixtures were centrifuged at 1,000 times g. for 5 minutes at room temperature and the supernatants were dialyzed for 36 hours against 25 liters of distilled water at room temperature. The dialysis bath was changed five times during a 24 hour period. This retentate was then used for testing. All specimens were run in duplicate.

Goat antisera monospecific for CEA material as diluated 1:2000 in 10% normal human serum and 0.05 M borate buffer pH 8.4. CEA material was prepared and labelled with $I^{125}$ as described in Example 1.

A dilution curve of the antisera against a constant amount of radioiodinated CEA material was carried out in the dialysates of perchloric acid serum extracts to which 1 ml. of borate buffer (0.05 M, pH 8.4) was added.

Six tubes of the serum were placed in a water bath at 45°C. for one-half hour. After incubation of the mixture, 5 ml. of ammonium acetate solution (0.1 M, pH 6.25) prepared by adjusting the pH of 0.1 M acetic acid to 6.25 with conc. $NH_4OH$, and 4 ml. of zirconyl phosphate gel (pH 6.25) were added to each tube and the tubes capped and inverted several times. The tubes were then centrifuged at 3,000 rpm for 15 minutes and the supernatants were discarded. The residue from each tube was resuspended in 10 ml. of ammonium acetate solution, recovered by centrifugation and assayed for bound $I^{125}$ in a gamma scintillation counter.

A titration curve was carried out by adding known amounts of unlabelled CEA material to the retentates of serum perchloric acid extracts. 1 Ml. borate buffer (pH 8.4, 0.5 M) and 0.5 ml. of a 1:1000 dilution of antisera was added to each of 6 tubes and incubated in a water bath at 45°C. for one-half hour. Then 0.1 ml. of radioiodinated CEA material containing 24,000 DPM was added to each specimen. The tubes were mixed well and reincubated for one-half hour. 5 Ml. of ammonium acetate solution (0.1 M pH 6.25) and zirconyl phosphate gel (pH 6.25) were then added to each tube. The tubes were capped, inverted several times and centrifuged at 1200 times g. for 15 minutes at room temperature. The supernatant was discarded and the gel precipitate was resuspended in 10 ml. ammonium acetate solution (0.1 M, pH 6.25). The gel was separated by centrifugation and assayed for bound $I^{125}$.

Specimens from patients were run in exactly the same manner as above except that unlabelled antigen was not added.

About 75% of the $I^{125}$ labelled material reacted with the antisera. A final dilution of 1:10,000 of the CEA-antisera in the perchloric acid extracts from serum reacts with 70% of the maximum amount of labelled antibody reactive material. The 1:10,000 dilution was therefore utilized.

Incubation of the antisera diluted with water (1:10,000) with unlabelled CEA material prior to addition of labelled antigen shows that the reaction of antibody with antigen is linear at antigen concentrations of from 1.5 to 10 ng./ml. but that the reaction is less sensitive at concentrations above 20 ng./ml.

Of 487 patients tested, those with carcinomas of the breast, lung colon had detectable concentrations of CEA material in their serum.

Of 229 patients without malignant disease, 11 had detectable antigen in their serum. Two of these later developed cancer, one had adenomatious polyp of the colon and 5 had severe emphysema.

EXAMPLE 8

1 ml. of plasma from suspected cancer patients was diluted with 4 ml. of physiological saline solution. An equal volume of 1.2 molar perchloric acid was added and the miture was agitated for 20 minutes then centrifuged at 8000 times gravity for 5 minutes at room temperature. The supernatant was collected and transferred to a dialysis tubing and dialyzed overnight against distilled water. The resulting retentate was dialyzed against an ammonium acetate solution of pH6to 6.25 containing 0.01 molar acetate, for 3 hours at room temperature. The retentate was transferred into 20 ml. test tubes. 30 Units of CEA antiserum was then added and the mixture incubated for 30 to 45 minutes at 45°C. 50 Ng. of CEA-$I^{125}$ containing 10,000 to 20,000 dpm./ng. was then added and the mixture incubated for 30 minutes at 45°C. 5 Ml. of pH 6.25 zirconyl phosphate gel was added to each test tube and 5 ml. of ammonium acetate solution (pH 6.25, 0.1 M) were then added. After mixing the tubes were centrifuged at 1500 times gravity for 5 minutes at room temperature and the resulting supernatant was discarded. The solid gel which remained was washed with the ammonium acetate buffer by filling the tubes with the buffer and dispersing the gel with a mixer, then centrifuging at 1500 times gravity for 5 minutes. The gel was assayed for bound $I^{125}$ with a Packard 3003 Tri-carb Scintillation Spectrometer. If CEA is present in the plasma, the amount of bound CEA-$I^{125}$ will be reduced proportionately.

EXAMPLE 9

10 Ml. of water were added to 0.1 ml. of plasma in a 20 ml. test tube. 30 Units of CEA antiserum were then added and the mixture incubated for 30–45 minutes at 45°C. 50 Ng. of CEA-$I^{125}$ containing 10,000 to 20,000 dpm./ng. were then added and the mixture incubated for 30 minutes at 45°C. 5 Ml. of pH 6.25 zirconyl phosphate gel and 5 ml. of ammonium acetate solution (pH 6.25, 0.01 M) were then added to each test tube. After mixing, the tubes were centrifuged at 1500 times gravity for 5 minutes at room temperature and the resulting supernatant was discarded. The solid gel which remained was washed with the ammonium acetate buffer by filling the tubes with the buffer and dispersing the gel with a mixer, then centrifuging at 1500 times gravity for 5 minutes. The gel was assayed for bound $I^{125}$ with a Packard 3003 Tri-carb Scintillation Spectrometer. If CEA is present in the plasma, the amount of bound CEA-$I^{125}$ will be reduced accordingly.

I claim:
1. A process for producing human carcinoembryonic antigen material, human carcinoembryonic antigen component A or human carcinoembryonic antigen component B which comprises
    a. homogenizing adenocarcinoma tissue;
    b. separating the solid particles from the homogenate;
    c. treating the supernatant with a glycoprotein solvent in which the carcinoembryonic antigen material, component A or component B is soluble;
    d. separating the precipitate and clarifying the resulting solution;
    e. dialyzing the clarified solution against a polyethylene glycol with an average molecular weight of about 15,000 to 20,000 and a softening point at 60°C.;
    f. dissolving the retentate in an aqueous buffer of pH from about 5 to 9;
    g. subjecting the resulting material to sequential chromatography on two different gel columns, the first of which is an agarose gel having about 6% by weight agarose and a particle size of from 40 to 210 microns and the second of which is a hydrophilic water-insoluble cross-linked dextran polymer gel;
    h. collecting and concentrating the eluates which have a spectrophotometric absorption peak wave length of 280 m$\mu$ and a molecular weight of about 200,000 to 500,000.
2. The process of claim 1 wherein prior to step (e) and subsequent to step (d), the clarified solution is dialyzed against distilled water.
3. The process of claim 1 wherein in step (g) the material is first dissolved in an aqueous buffer of about pH 7 then run through the agarose gel column which separates the CEA material, component A or component B containing fraction from higher and lower molecular weight material and colloidal particles, the eluates having a molecular weight ranging from about 200,000 -500,000 and a reading with a peak at 280 m$\mu$ on a UV spectrophotometer are collected, dialyzed against polyethylene glycol of molecular weight about 20,000, the retentate dissolved in an aqueous buffer of pH about 7 and run through a cross-linked dextran gel column which has a higher resolving power than the first column and separates CEA material, component A or component B containing fraction from higher and lower molecular weight material.

* * * * *